United States Patent [19]

Weston

[11] 4,294,843

[45] Oct. 13, 1981

[54] ANTI-PROTOZOAL OXADIAZOLE DERIVATIVES

[75] Inventor: John B. Weston, Tring, England

[73] Assignee: Burroughs Wellcome Co., Research Triangle Park, N.C.

[21] Appl. No.: 56,998

[22] Filed: Jul. 12, 1979

[30] Foreign Application Priority Data

Jul. 13, 1978 [GB] United Kingdom ............... 29817/78

[51] Int. Cl.³ ..................... A61K 31/42; C07D 271/06
[52] U.S. Cl. ..................................... 424/272; 548/131
[58] Field of Search ......................... 548/131; 424/272

[56] References Cited

U.S. PATENT DOCUMENTS

| 3,897,447 | 7/1975 | Fisher et al. | 548/131 |
| 4,067,988 | 1/1978 | Buret et al. | 548/131 |
| 4,148,801 | 4/1979 | Santilli et al. | 548/131 |

FOREIGN PATENT DOCUMENTS

| 8356 | 3/1980 | European Pat. Off. | |
| 2219841 | 10/1973 | Fed. Rep. of Germany | 548/131 |
| 2347926 | 11/1977 | France | 548/131 |

OTHER PUBLICATIONS

Rochling, et al., "Liebigs Ann. Chem.", 1974, 504–522.
Jaunin, "Chem. Abst.", vol. 64, (1966), p. 11197.
Derwent Abstract 81163X/44 and Othen.
Haynes et al., "J. Med. Chem.", vol. 15, No. 11, (1972), pp. 1198–2000.

Primary Examiner—Anton H. Sutto
Attorney, Agent, or Firm—Donald Brown

[57] ABSTRACT

Anti-protozoal 1,2,4-oxadiazole derivatives of the formula:

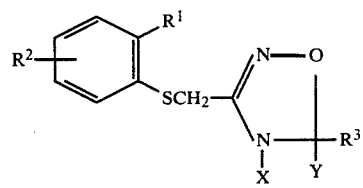

wherein $R^1$ is amino or substituted amino; each $R^2$ is the same or different in one or more of the 3, 4, 5 or 6 positions and is hydrogen, lower alkyl, halogen, hydroxy, alkoxy, alkylthio, arylthio, amino, substituted amino, cyano or nitro; X and Y together represent a bond or X and Y are both hydrogen; $R^3$ is hydrogen, lower alkyl, aryl, substituted aryl or $ArS.CH_2$—; and Ar is unsubstituted or mono-, di- or tri-substituted phenyl wherein the substituents may be the same of different, and acid addition salts thereof, methods for their preparation, formulations thereof and their use in the treatment of protozoal infections, especially malaria are described.

17 Claims, No Drawings

ANTI-PROTOZOAL OXADIAZOLE DERIVATIVES

The present invention relates to novel chemical compounds, intermediates therefor, methods for their preparation, formulations containing them and to their use in human and veterinary medicine.

More particularly the invention is concerned with 1,2,4-oxadiazole derivatives of formula (I) below which have been found to be active against protozoa, in particular against protozoa of the genus Plasmodium in mice and of the genus Eimeria in chicks. The compounds of formula (I) are thus of use in the treatment or prophylaxis of protozoal infections amongst which are included malaria in mammals (including man) and of coccidiosis in poultry.

Compounds of formula (I) are:

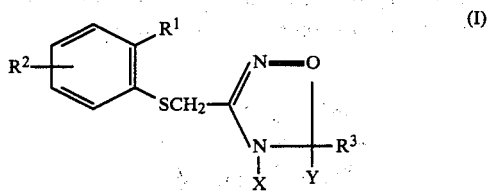

wherein $R^1$ is amino or substituted amino; each $R^2$ is the same or different, in one or more of the 3,4,5- or 6-positions of the phenyl ring, and is selected from hydrogen, lower alkyl, halogen, hydroxy, alkoxy, alkylthio, arylthio, amino, substituted amino, cyano or nitro;

X and Y together represent a bond or X and Y are both hydrogen;

$R^3$ is hydrogen, lower alkyl, aryl, substituted aryl, or a group —$CH_2$—S—Ar; and Ar is unsubstituted or mono-, di- or trisubstituted phenyl wherein the substituents may be the same or different, and acid addition salts thereof.

Lower alkyl as used herein refers to an alkyl group having from 1 to 6 carbon atoms.

Substituted amino as used herein refers to a group —$NH_2$ where one or both of the hydrogen atoms is/are replaced by one or more residues containing carbon, hydrogen and, optionally, one or more of oxygen, nitrogen, sulphur and halogen.

Substituted amino thus includes for example, alkylamino (e.g. NHMe; NMe$_2$), arylamino (e.g. —NHPh); aralkylamino (e.g. —NHCH$_2$ Ph; —NHCH$_2$C$_6$H$_4$Cl), amido, (e.g. —NHCOMe; NHCOPh; —NHCOC$_6$H$_4$Cl; —NHCOC$_6$H$_4$OMe; —NHCOCMe$_3$), alkoxylcarbonylamino (e.g. —NHCO$_2$Me; —NHCO$_2$Et; NHCO$_2$CH$_2$Ph), sulphonamido (e.g. —NHSO$_2$Me; —NH.SO$_2$C$_6$H$_4$.Me), ureido (e.g. —NHCONHC$_6$H$_{11}$; —NHCONHPh), thioureido (e.g. —NHCSNHPh; —NHCSNHCO$_2$Et; —NHCSNHC$_6$H$_4$OC$_6$H$_4$NO$_2$; —NHCSNHC$_6$H$_4$NO$_2$), imino (e.g. —N=CHC$_6$H$_4$OMe; —N=CHC$_6$H$_3$(OMe)$_2$; —N=CH-C$_6$H$_4$Cl) and substituted alkylamino (e.g. —NH(CH$_2$)$_n$NR$_2$ where n is an integer, suitably 1 to 4, and R is lower alkyl).

The anti-protozoal activity of the compounds of formula (I) resides in the free base and thus the nature of the acid participating in the acid addition salts is of minor importance. In the preparation of the compounds of the invention acid addition salts of any kind may be prepared. However when the compounds of formula (I) are to be used in therapy the salts are preferably derived from non-toxic acids. The acids used will normally be those recognised to give pharmaceutically or veterinarily acceptable acid addition salts. Such acid addition salts include, for example, those derived from hydrochloric acid, hydroiodic acid, sulphuric acid, p-toluenesulphonic acid, maleic acid, lactic acid, citric acid, tartaric acid, succinic acid, oxalic acid and p-chlorobenzenesulphonic acid.

Compounds of formula (I) of particular interest are those wherein $R^2$ is hydrogen. More particularly of interest are compounds of formula (II):

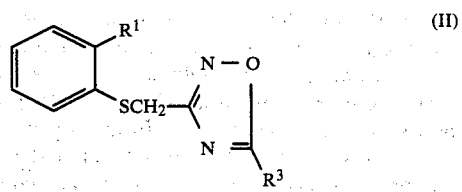

wherein $R^1$ and $R^3$ are as defined in formula (I) and notably those compounds wherein $R^3$ is hydrogen. Particularly valuable compounds of formula (I) include:

3-(2-Aminophenylthiomethyl)-1,2,4-oxadiazole;
3-(2-Ethoxycarbonylaminophenylthiomethyl)-1,2,4-oxadiazole;
3-(2-Methoxycarbonylaminophenylthiomethyl)-1,2,4-oxadiazole;
3-(2-Benzyloxycarbonylaminophenylthiomethyl)-1,2,4-oxadiazole;
3-(2-Benzamidophenylthiomethyl)-1,2,4-oxadiazole;
3-[2-(4-Methoxybenzamido)phenylthiomethyl]-1,2,4-oxadiazole;
3-[2-(4-Chlorobenzamido)phenylthiomethyl]-1,2,4-oxadiazole;
3-(2-Methylaminophenylthiomethyl)-1,2,4-oxadiazole;
3-(2-Dimethylaminophenylthiomethyl)-1,2,4-oxadiazole;
3-[2-(3,4-Dimethoxybenzylideneamino)phenylthiomethyl]-1,2,4-oxadiazole;
3-[2-(4-Methoxybenzylideneamino)phenylthiomethyl]oxadiazole;
3-(2-Amino-4-methylphenylthiomethyl)-1,2,4-oxadiazole;
3-(2-Amino-5-methylphenylthiomethyl)-1,2,4-oxadiazole; and
3-(2-Aminophenylthiomethyl)-4,5-dihydro-1,2,4-oxadiazole.

The compounds of formula (I) and their acid addition salts may be prepared by any method known in the art for the preparation of compounds of analogous structure. In the following discussion of particular methods for the preparation of the compounds of formula (I) it should be understood that where an intermediate has more than one reactive nitrogen atom it is desirable that the nitrogen atom which is not intended to participate in the reaction be blocked by a suitable protecting group.

In particular compounds of formula (I) may be prepared by the reaction of an amidoxime of formula (III) (which are themselves novel compounds and form a further aspect of the invention).

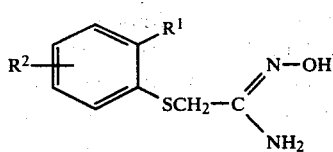 (III)

where R¹ and R² are as defined in formula (I) above, either with an acylating agent of formula (IV):

R³COZ  (IV)

where R³ is as defined in formula (I) above and Z is a leaving group, to give compounds where X and Y represent a bond; or an aldehyde or source thereof (e.g. formaldehyde or paraformaldehyde), to give a compound where X and Y are both hydrogen.

The reaction may be carried out under conditions known in the art for conducting the Tiemann acylation synthesis. Thus suitable acylating agents include unsubstituted or substituted orthoesters, esters, carboxylic acids, carboxylic acid anhydrides and acid halides. The reaction may be effected in the absence or presence of an inert organic solvent (such as benzene or toluene) and is preferably effected at temperatures in the range of 60° to 200° C.

When the acylating agent is an orthoester the reaction is preferably carried out in the presence of an acid catalyst such as a mineral acid (e.g. sulphuric acid) or Lewis acid (e.g. boron trifluoride). When the acylating agent is an acyl halide the reaction is preferably conducted in the presence of an inorganic or organic base (e.g. trimethylamine).

It will of course be understood that in conducting this reaction the intermediate acyl compound of formula (V) may be formed.

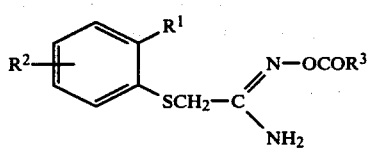 (V)

This compound may either be converted in situ to a compound of formula (I) or may be isolated and further reacted under suitable conditions to give a compound of formula (I).

The compounds of formula (V) are themselves novel compounds and form a further aspect of the invention. Compounds of formula (III) of particular interest are those which lead to compounds of formula (II) above. Notable compounds of formula (III) include:
2-(2-Aminophenylthio)acetamidoxime; and
2-(2-Dimethylaminophenylthio)acetamidoxime.

Compounds of formula (I) where R³ is hydrogen or lower alkyl may be prepared by the reaction of a compound of formula (VI):

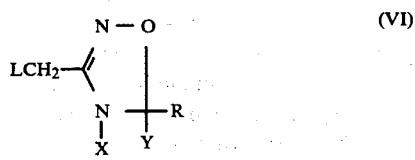 (VI)

where L is a leaving group, e.g. halogen, R is hydrogen or lower alkyl and X and Y are as defined above, with a thiophenol of formula (VII):

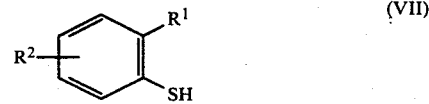 (VII)

where R¹ and R² are as defined in formula (I) above; L is preferably chloro and the reaction is suitably carried out in the presence of an alkali metal (e.g. sodium) in an aliphatic alcohol (e.g. ethanol), preferably at ambient temperature.

Compounds of formula (I) where R¹ is substituted amino may be prepared from the corresponding unsubstituted amino compound of formula (VIII):

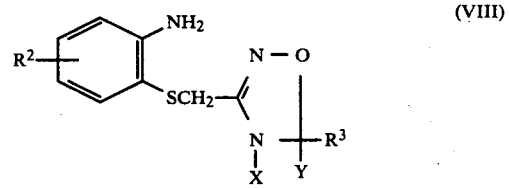 (VIII)

where R², R³, X and Y are as defined in formula (I) above by methods known in the art for the conversion of the group —NH₂ to substituted amino groups. Suitable reagents for conversion of compounds of formula (VIII) to such compounds of formula (I) include alkylating agents (to give alkylamines), aralkylating agents (to give aralkylamines) acylating agents (to give amides), sulphonylating agents (to give sulphonamides), isocyanates or isothiocyanates (to give ureido or thioureido compounds) and aldehydes or aldehyde acetals (to give amino compounds). Such reactions may suitably be carried out in inert solvents (e.g. benzene, toluene) at elevated temperatures.

Compounds of formula (I) wherein R³ is a group Ar—S—CH₂— may be prepared by the reaction of a compound of formula (IX):

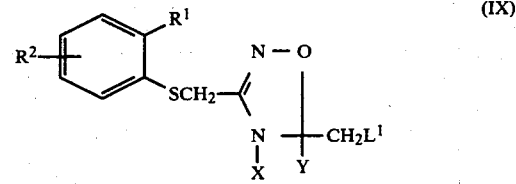 (IX)

where R¹, R², X and Y are as defined in formula (I) and L¹ is a leaving group e.g. halogen (preferably chloro) with a thiophenol ArSH (where Ar is as defined in formula (I) above). The reaction conditions are suitably those used for the conversion of a compound of formula (VI) to a compound of formula (I).

Compounds of formula (I) wherein R³ is a methylthiophenyl group, which may be represented the formula (X):

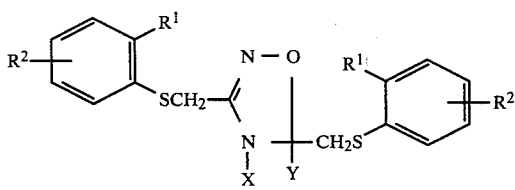

where $R^1$, $R^2$, X and Y are as defined in formula (I) above, may be prepared by the reaction of a compound of formula (XI):

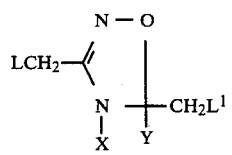

where L and $L^1$ are both leaving groups, e.g. halogen (preferably chloro) with two molar equivalents of a thiophenol of formula (VII) to give a compound of formula (I).

Compounds of formula (I) where X and Y are both hydrogen may be prepared by reaction of an oxadiazole analogue of formula (I) where X and Y represent a bond with a reducing agent, notably sodium borohydride. The reaction may conveniently be carried out in an aliphatic alcohol, e.g. methanol, at elevated or, preferably, ambient temperature.

Acid addition salts of the compounds of formula (I) may be prepared by any method known in the art for the preparation of such salts of analogous compounds. In particular they may be prepared by treatment of the free base with an appropriate acid or by methathesis.

While it is possible that, for use as antiprotozoal agents, the compounds of formula (I) and their non-toxic acid addition salts (hereinafter referred to as "the active compounds") may be administered as the raw chemical it is preferable to present the active ingredient(s) as a pharmaceutical or veterinary formulation.

Pharmaceutical formulations comprise the active compound(s) together with one or more pharmaceutically acceptable carriers therefor and optionally other therapeutic and/or prophylactic ingredients. The carrier(s) must be "acceptable" in the sense of being compatible with the other ingredients of the formula and not deleterious to the recipient thereof.

It will be appreciated that the amount of active compound required for use in the treatment or prophylaxis of protozoal infections will vary not only with the nature of the active compound but also with the route of administration and the nature of the infection to be controlled. In general a suitable dose for a mammal (including man) for the treatment of protozoal infections, for example malaria, will lie in the range of 0.1 mg to 200 mg base/kilogram body weight, with a preferred range of 1 to 100 mg.

The active compound(s) may conveniently be presented (as a pharmaceutical formulation) in unit dosage form. A convenient unit dose formulation contains the active compound(s) in an amount of from 10 mg to 1g.

The pharmaceutical formulations include those suitable for oral, rectal or parenteral (including intramuscular and intravenous) administration, although oral is the preferred route. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the active compound, either alone or in admixture with one or more accessory ingredients, into the capsule cases and then sealing them in the usual manner. Cachets are analogues to capsules wherein the active ingredient together with any accessory ingredient(s) is sealed in a rice paper envelope.

Pharmaceutical formulations suitable for oral administration wherein the carrier is a liquid may be presented as a solution or a suspension in an aqueous liquid or a non-aqueous liquid, or as an oil-in-water or water-in-oil liquid emulsion.

Pharmaceutical formulations suitable for rectal administration wherein the carrier is a solid are most preferably as unit dose suppositories. Suitable carriers include cocoa butter and other materials commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The veterinary formulations of the present invention are normally in either powder or liquid concentrate form. In accordance with standard veterinary formulation practice, conventional water soluble excipients such as lactose or sucrose, may be incorporated in the powders to improve their physical properties. Thus particularly suitable powders of this invention comprise 50 to 100% w/w, and preferably 60 to 80% w/w of the active ingredient(s), and 0 to 50% w/w and preferably 20 to 40% w/w of conventional veterinary exipients. These powders may either be added to animal feedstuffs, for example by way of an intermediate premix, or diluted in animal drinking water.

Liquid concentrates of this invention suitably contain a water soluble compound of formula (I) or a veterinarily acceptable water soluble salt and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following Examples are given purely by way of illustration of the present invention and should not be construed in any way as constituting a limitation thereof. All temperatures are in degrees Celsius.

EXAMPLE 1

3-(2-Dimethylaminophenylthiomethyl)-1,2,4-oxadiazole

A mixture of 2-(2-dimethylaminophenylthio)acetamidoxime (1.0 g), triethylorthoformate (1.5 ml) and boron trifluoride etherate (0.015 ml) was warmed at 70° whence a solution soon formed. Heating at 70° was continued for 5 hours, the reaction mixture cooled and solvent removed by evaporation under reduced pressure. The residual oil was taken up in diethyl ether, washed with 5% aqueous sodium carbonate solution and water, dried and evaporated to dryness under reduced pressure. The residue was distilled under reduced pressure to give 3-(2-dimethylaminophenylthiomethyl)-1,2,4-oxadiazole as a colourless oil, b.p. 119° (0.07 mm Hg).

EXAMPLE 2

3-(2-Dimethylaminophenylthiomethyl)-5-phenyl-1,2,4-oxadiazole a. Preparation of O-benzoyl-2-(2-dimethylaminophenylthio)acetamidoxime Benzoyl chloride (1.41 g 0.01 mol) in benzene (10 ml) was added dropwise to a stirred mixture of 2-(2-dimethylaminophenylthio)acetamidoxime (2.25 g, 0.01 mol) and triethylamine (1.01 g, 0.01 mol) in benzene (50 ml). Stirring was continued for a further 12 hours and a pale yellow crystalline material removed by filtration and washed with hexane. The crude product was recrystallised from isopropanol to give the product as pale yellow needles, m.p. 134° to 135°.

b. Preparation of 3-(2-dimethylaminophenylthiomethyl)-5-phenyl-1,2,4-oxadiazole

O-Benzoyl-2-(2-dimethylaminophenylthio)acetamidoxime (0.5 g, $1.5 \times 10^{-3}$ mol) was heated in toluene (10 ml) at reflux with boron trifluoride etherate (2 drops) for 1½ hours. The brown solution thus obtained was mixed with ether and saturated aqueous sodium bicarbonate solution. Ether extraction gave a brown oil which was purified by chromatography on silica gel (30 g), elution with ether/hexane (1:2) giving 3-(2-dimethylaminophenylthiomethyl)-5-phenyl-1,2,4-oxadiazole, m.p. 100.5°.

EXAMPLE 3

3-(2-Aminophenylthiomethyl)-1,2,4-oxadiazole

Sodium (1.27 g; 0.055 mol) was dissolved in absolute ethanol (50 ml) and to this was added 2-aminothiophenol (7.38 g; 0.059 mol). To the resulting solution was added 3-chloromethyl-1,2,4-oxadiazole (6.59 g; 0.055 mol) dropwise over 10 minutes. The resulting mixture was then stirred at ambient temperature for 30 minutes, sodium chloride removed by filtration and the filtrate was evaporated to dryness under reduced pressure to give 3-(2-aminophenylthiomethyl)-1,2,4-oxadiazole which was re-crystallised from isopropanol; m.p. 57°.

EXAMPLES 4 to 18

By methods analogous to that described in Example 1 the following compounds were also prepared:

EXAMPLE 4

3-(2-Methylaminophenylthiomethyl)-1,2,4-oxadiazole, m.p. 77°.

EXAMPLE 5

3-(2-Dimethylaminophenylthiomethyl)-1,2,4-oxadiazole, b.p. 132° (0.2 mm Hg), identical to the product of Example 1.

EXAMPLE 6

3-(2-Amino-4-methylphenylthiomethyl)-1,2,4-oxadiazole, m.p. 25°.

EXAMPLE 7

3-(2-Amino-5-methylphenylthiomethyl)-1,2,4-oxadiazole, m.p. 54°.

EXAMPLE 8

3-(2-Amino-4-chlorophenylthiomethyl)-1,2,4-oxadiazole, m.p. 50°.

EXAMPLE 9

3-(2-Amino-6-chlorophenylthiomethyl)-1,2,4-oxadiazole, m.p. 74°.

EXAMPLE 10

3-(2-Amino-4-bromophenylthiomethyl)-1,2,4-oxadiazole, m.p. 48°.

EXAMPLE 11

3-(2-Aminophenylthiomethyl)-5-(4-chlorophenyl)-1,2,4-oxadiazole, m.p. 127°.

EXAMPLE 12

3-(2-Aminophenylthiomethyl)-5-methyl-1,2,4-oxadiazole, m.p. 174°–175°.

EXAMPLE 13

3,5-Di-(2-aminophenylthiomethyl)-1,2,4-oxadiazole, m.p. 68°.

EXAMPLE 14

3-(2-Aminophenylthiomethyl)-5-phenyl-1,2,4-oxadiazole, m.p. 141°.

EXAMPLE 15

3-(2-Aminophenylthiomethyl)-5-methyl-1,2,4-oxadiazole hydrochloride, m.p. 174.5° (decomposition).

EXAMPLE 16

3-(2-Amino-4-fluorophenylthiomethyl)-1,2,4-oxadiazole m.p. 66°–66.5°.

EXAMPLE 17

3-(2-Dimethylamino-4-methoxyphenylthiomethyl)-1,2,4-oxadiazole, colourless oil, mass spectrum M+1 266; refractive index 1.5830.

EXAMPLE 18

3-(4-Chloro-2-dimethylaminophenylthiomethyl)-1,2,4-oxadiazole, colourless oil, mass spectrum M+1 270; refractive index 1.6005.

EXAMPLE 19

3-(2-Ethoxycarbonylaminophenylthiomethyl)-1,2,4-oxadiazole

A solution of ethyl chloroformate (0.55 g) in benzene (10 ml) was added dropwise to a solution of 3-(2-aminophenylthiomethyl)-1,2,4-oxadiazole (2.07 g) in benzene (10 ml). The reaction mixture was then stirred for 2 days, filtered and the filtrate evaporated under reduced pressure to give an oil which crystallised on standing. Re-crystallisation from isopropanol gave 3-(2-ethoxycarbonylaminophenylthiomethyl)-1,2,4-oxadiazole, m.p. 55°.

EXAMPLE 20

A method analogous to that used in Example 19 yielded 3-(2-methoxycarbonylaminophenylthiomethyl)-1,2,4-oxadiazole, m.p. 52°.

EXAMPLE 21

3-(2-Benzyloxycarbonylaminophenylthiomethyl)-1,2,4-oxadiazole

A solution of benzylchloroformate (3.79 g) and 3-(2-aminophenylthiomethyl)-1,2,4-oxadiazole (3.1 g) in dioxan (75 ml) containing potassium carbonate (3.15 g) was refluxed for 1 hour. Solvent was then removed by evaporation under reduced pressure to give a colourless solid which was re-crystallised from hexane to give 3-(2-benzyloxycarbonylaminophenylthiomethyl)-1,2,4-oxadiazole, m.p. 41°.

EXAMPLE 22

A method analogous to that used in Example 21 but using 3-(2-methylaminophenylthiomethyl)-1,2,4-oxadiazole as the starting material yielded 3-[2-(N-benzyloxy carbonyl-N-methyl)aminophenythiomethyl]-1,2,4-oxadiazole mass spectrum M+1 356; refractive index 1.5905

EXAMPLE 23

3-(2-Acetylaminophenylthiomethyl)-1,2,4-oxadiazole 3-(2-Aminophenylthiomethyl)-1,2,4-oxidiazole (3.1 g) and acetic anhydride (1.53 g) in acetic acid (25 ml) was stirred at ambient temperature for 30 minutes. The solvent was then removed by evaporation under reduced pressure to yield an oil which crystallised on cooling. Re-crystallisation from isopropanol gave 3-(2-acetylaminophenylthiomethyl)-1,2,4-oxadiazole, m.p. 89°.

EXAMPLE 24

By the method of Example 23 was prepared 3-[2-(3-carboxyproprionamido)phenylthiomethyl]1,2,4-oxadiazole, m.p. 91°.

EXAMPLE 25

3-[2-(4-Chlorobenzamido)phenylthiomethyl]1,2,4-oxadiazole

A mixture of 3-(2-aminophenylthiomethyl)1,2,4-oxadiazole (4.14 g), 4-chlorobenzoyl chloride (3.68 g), sodium hydroxide (0.8 g) and water (15 ml) was stirred at 25° for 4 hours. Crude product was recovered by filtration and crystallised from ethanol to give 3-[2-(4-chlorobenzamido)phenylthiomethyl]-1,2,4-oxadiazole, m.p. 103°.

By methods analogous to that used in Example 25 the compounds of Examples 26 to 30 were prepared.

EXAMPLE 26

3-(2-Benzamidophenythiomethyl)-1,2,4-oxadiazole, m.p. 101.5°.

EXAMPLE 27

3-[2-(4-Methoxybenzamido)phenylthiomethyl]-1,2,4-oxadiazole, m.p. 94°.

EXAMPLE 28

3-(2-Trimethylacetamidophenylthiomethyl)1,2,4-oxadiazole, m.p. 140°.

EXAMPLE 29

3-(2-Furanoylaminophenylthiomethyl)1,2,4-oxadiazole, m.p. 107°.

EXAMPLE 30

3-(Thiophene-2-carbonylaminophenylthiomethyl)1,2,4-oxadiazole, m.p. 98°.

EXAMPLE 31

3-(2-Methylsulphonamidophenylthiomethyl)-1,2,4-oxadiazole

Methanesulphonyl chloride (1.39 g) was added dropwise to a cooled solution of 3-(2-aminophenylthiomethyl)-1,2,4-oxadiazole (3.1 g) in pyridine (12 ml). The reaction mixture was then poured into water (75 ml) the so formed solid removed by filtration and crystallised from ethanol to give 3-(2-methylsulphonamidophenylthiomethyl)-1,2,4-oxadiazole, m.p. 106°.

EXAMPLE 32

By the method of Example 31 was prepared 3-[2-(p-toluenesulphonamido)phenylthiomethyl]-1,2,4-oxadiazole, m.p. 139°.

EXAMPLE 33

N-[2-(1,2,4-Oxadiazol-3-yl-methylthiophenyl]-N$^1$-phenylthiourea

Phenylisothiocyanate (1.31 g) in benzene (10 ml) was added dropwise to a stirred solution of 3-(2-aminophenylthiomethyl)-1,2,4-oxadiazole (20 g) in benzene (10 ml). The resultant solution was refluxed for 3 hours, the solvent removed by evaporation under reduced pressure to give a solid which was re-crystallised from isopropanol to give N-[2-(1,2,4-oxadiazol-3-yl-methylthio)phenyl]-N$^1$-phenylthiourea, m.p. 128°.

By method of Example 33 the compounds of Example 34 to 38 were prepared.

EXAMPLE 34

N-[2-(1,2,4-oxadiazol-3-yl-methylthio)phenyl]-N$^1$-phenyl urea, m.p. 58°.

EXAMPLE 35

N-[2-(1,2,4-oxadiazol-3-yl-methylthio)phenyl]-N[1]-cyclohexyl urea, m.p. 99°.

EXAMPLE 35

N-[2-(1,2,4-oxadiazol-3-yl-methylthio)phenyl]-N[1]-ethoxycarbonyl thiourea, m.p. 149°.

EXAMPLE 36

N-[2-(1,2,4-oxadiazol-3-yl-methylthio)phenyl]-N[1]-4-(4-nitrophenyloxy)phenyl thiourea, m.p. 157°.

EXAMPLE 37

N-[2-(1,2,4-oxadiazol-3-yl-methylthio)phenyl]-N[1]-4-(4-nitrophenylthio)phenyl thiourea, m.p. 166°.

EXAMPLE 38

3-[2-(3,4-Dimethoxybenzylideneamino)phenylthiomethyl]-1,2,4-oxadiazole

A solution of 3-(2-aminophenylthiomethyl)1,2,4-oxadiazole (4.2 g) in 3,4-dimethoxybenzaldehyde diethyl acetal (9.6 g) was heated under reflux for 30 minutes. On cooling and the addition of hexane yellow crystals precipitated. These were removed by filtration and re-crystallised from ethanol to give 3-[2-(3,4-dimethoxybenzylideneamino)phenylthiomethyl]-1,2,4-oxadiazole, m.p. 146°.

By methods analogous to that used in Example 38 the compounds of Examples 39 to 41 were prepared.

EXAMPLE 39

3-[2-(4-Methoxybenzylideneamino)phenylthiomethyl]-1,2,4-oxadiazole, m.p. 62°.

EXAMPLE 40

3-[2-(2-Chlorobenzylideneamino)phenylthiomethyl]-1,2,4-oxadiazole, m.p. 87°.

EXAMPLE 41

3-[2-(3,4,5-Trimethoxybenzylideneamino)phenylthiomethyl]-1,2,4-oxadiazole, m.p. 167°.

EXAMPLE 42

3-[2-(4-Chlorobenzylamino)phenylthiomethyl]1,2,4-oxadiazole

4-Chlorobenzyl chloride (4.0 g; $2.5 \times 10^{-2}$ mol) was added dropwise to a stirred mixture of 3-(2-aminophenylthiomethyl)-1,2,4-oxadiazole (5.2 g; $2.5 \times 10^{-2}$ mol), sodium hydrogen carbonate (2.1 g; $2.5 \times 10^{-2}$ mol) and sodium iodide (0.38 g; $2.5 \times 10^{-3}$ mol) in water (25 ml). The reaction mixture was stirred at ambient temperature for 2 weeks, extracted with ether ($3 \times 50$ ml), the extracts dried over magnesium sulphate and evaporated under reduced pressure to yield crude product. Re-crystallisation from isopropanol gave 3- 2-(4-chlorobenzylamino)phenylthiomethyl -1,2,4-oxadiazole, m.p. 84°.

EXAMPLE 43

2-Hydroxy-1-[2-(1,2,4-oxadiazol-3-ylmethylthio)anilino]-3-phenoxypropane

A mixture of 3-(2-aminophenylthiomethyl)1,2,4-oxadiazole (2.07 g; $10^{-2}$ mol) and 1,2-epoxy-3-phenoxy propane (1.5 g; $10^{-2}$ mol) was warmed on a steam bath during 48 hours. The so produced mixture was chromatographed on silica gel, elution with diethyl ether/hexane (1:1) producing 2-hydroxy-1-[2-(1,2,4-oxadiazol-3-yl-methylthio)anilino]-3-phenoxypropane as a colourless oil.

EXAMPLE 44

3-[2-(2-Nitrophenylsulphenylamino)phenyl]thiomethyl-1,2,4-oxadiazole

A solution of 2-nitrophenylsulphenyl chloride (1.44 g, $7.5 \times 10^{-3}$ mol) in chloroform was added dropwise to a solution of 3-(2-aminophenylthiomethyl)-1,2,4-oxadiazole in chloroform (20 ml). The yellow mixture was stirred overnight, the crude product collected by filtration and recrystallised from ethyl acetate/hexane to give 3-[2-(2-nitrophenylsulphenylamino)phenyl]thiomethyl-1,2,4-oxadiazole, m.p. 90° (dec.).

EXAMPLE 45

3-(2-Diethylaminophenylthiomethyl)-1,2,4-oxadiazole

A mixture of diethyl sulphate (25.9 g, 0.168 mol), 3-(2-aminophenylthiomethyl)-1,2,4-oxadiazole (9.96 g, 0.0481 mol), sodium bicarbonate (16.08 g, 0.192 mol) and water (25 ml) was stirred for 1 month at 25°. The reaction was extracted with ether and the pale yellow oil thus obtained purified by column chromatography on silica gel (150 g). Elution with ether:hexane (2:3) gave the desired product as a pale yellow oil, mass spectrum M+1 264; refractive index 1.5590.

EXAMPLE 46

By the method of Example 45 and using 3-(2-methylaminophenylthiomethyl)-1,2,4-oxadiazole, 3-[2-(N-ethyl-N-methyl)aminophenylthiomethyl]1,2,4-oxadiazole, (mass spectrum M+1 250; refractive index 1.5801) was prepared.

EXAMPLE 47

5-(4-Bromophenylthiomethyl)-3-(2-dimethylaminophenylthiomethyl)-1,2,4-oxadiazole A. Chloroacetylchloride (2.64 ml, 3.74 g, $3.3 \times 10^{-2}$ mol) in benzene (10 ml) was added dropwise to a stirred solution of 2-(2-dimethylaminophenylthio)acetamidoxime (6.75 g, 0.03 mol) and triethylamine (4.17 ml) in benzene (20 ml). The mixture was stirred at ambient temperature for 10 hours then refluxed for 1 hour. The cooled mixture was taken up in ether and 5% aqueous sodium bicarbonate solution. The organic layer was washed with water and saturated aqueous sodium chloride solution dried and evaporated to dryness to give a brown oil. Chromatography on silica gel (135 g), eluting with hexane:ether (3:1) gave 5-(chloromethyl)-3-(2-dimethylaminophenylthiomethyl)-1,2,4-oxadiazole as a colourless oil, nmr δ(CDCl$_3$) 2.78(6H, CH$_3$), 4.20(2H, ,—CH$_2$—), 4.65 (2H, ,—CH$_2$—), 6.8-7.4 (4H, m, aromatic hydrogens).

B. Sodium methoxide, (0.27 g, $4.9 \times 10^{-3}$ mol) was dissolved in methanol with cooling and stirring. When 4-bromobenzenethiol (0.93 g, $4.9 \times 10^{-3}$ mol) had dissolved in this solution, 5-chloromethyl-3-(2-dimethylaminophenylthio)-1,2,4-oxadiazole (1.4 g, $4.9 \times 10^{-3}$ mol) was added. The solution was filtered and the solvent removed from the filtrate to give a solid which on re-crystallisation from isopropanol gave colourless flakes of 5-(4-kromoxhenylthiomethyl)-3-(2-dimethylaminophenylthiomethyl)-1,2,4-oxadiazole, m.p. 78°.

EXAMPLE 48

By a method analogous to that used in Example 47 was prepared 5-(4-chlorophenylthiomethyl)-3-(2-dimethylaminophenylthiomethyl)-1,2,4-oxadiazole, m.p. 93°.

EXAMPLE 49

3,5-Di-(2-aminophenylthiomethyl)-1,2,4-oxadiazole

2-Aminobenzenethiol (5.0 g, 0.04 mol) was dissolved in a solution of sodium (0.92 g, 0.04 mol) in ethanol (50 ml) and 3,5-di(chloromethyl)-1,2,4-oxadiazole (3.3 g, 0.02 mol) was added. After filtration of the mixture, the filtrate was collected and the solvent removed to yield the crude product which on re-crystallisation from isopropanol gave 3,5,-di-(2-aminophenylthiomethyl)-1,2,4-oxadiazole, m.p. 68°.

EXAMPLE 50

By the method of Example 49 3,5-di-(2-amino-4-chlorophenylthiomethyl)-1,2,4-oxadiazole, m.p. 82°, was prepared.

EXAMPLE 51

3-(2-Aminophenylthiomethyl)-4,5-dihydro-1,2,4-oxadiazole

To a solution of 3-(2-aminophenylthiomethyl)1,2,4-oxadiazole (3.1 g, 0.015 mol) in dry methanol was added sodium borohydride (1.72 g) at 0° in aliquots over 2 hours, with stirring. After standing at 0° overnight a white precipitate had formed. The crude product was recovered by filtration and re-crystallised from ethanol to give 3-(2-aminophenylthiomethyl)-4,5-dihydro-1,2,4-oxadiazole, m.p. 108°.

By a method analogous to that described in Example 51 the compounds of Examples 52 and 53 were prepared.

EXAMPLE 52

3-(2-Amino-4-chlorophenylthiomethyl)-4,5-dihydro-1,2,4-oxadiazole, m.p. 148°.

EXAMPLE 53

3-(2-Dimethylaminophenylthiomethyl)-4,5-dihydro-1,2,4-oxadiazole, mass spectrum M+1 238, refractive index 1.6084.

EXAMPLE 54

3-(2-Aminophenylthiomethyl)-1,2,4-oxadiazole hydrochloride

A stream of hydrogen chloride was passed, at ambient temperature, through a solution of 3-(2-aminophenylthiomethyl)-1,2,4-oxadiazole (10 g) in dry diethylether (250 ml) until no further precipitation resulted. The colourless precipitate was collected by filtration, washed with diethyl ether and crystallised from ethanol to give 3-(2-aminophenylthiomethyl)-1,2,4-oxadiazole hydrochloride, m.p. 147°.

EXAMPLE 55

2-(2-Aminophenylthio)acetamidoxime

2-Aminobenzenethiol (3.75 g, 0.03 mol) was added to a solution of sodium (0,06 mol, 1.38 g) in ethanol (50 ml). Solid chloroacetamidoxime hydrochloride (4.35 g, 0.03 mol) was added in one portion. After stirring for 10 minutes the reaction mixture was filtered and the filtrate evaporated to dryness to give the crude product which was re-crystallised from iso-propanol to give 2-(2-aminophenylthio) acetamidoxime, m.p. 80°.

EXAMPLE 56

2-(2-Dimethylaminophenylthio)acetamidoxime

2-Dimethylaminobenzenethiol (4.6 g; $3 \times 10^{-2}$ mol) was added dropwise to a solution of sodium (0.69 g; $3 \times 10^{-2}$ mol) in absolute ethanol (50 ml) at 25°. Immediately chloroacetamidoxime was added. Stirring at 25° was continued for 2 hours, sodium chloride was removed by filtration and the filtrate evaporated under reduced pressure. Re-crystallisation of the residue from isopropanol gave 2-(2-dimethylaminophenylthio)acetamidoxime, m.p. 133°.

EXAMPLE 57

Groups of five mice were inoculated intraperitoneally with the normal strain of *P. berghei*. The mice on test received seven oral doses of drug beginning on the afternoon of the day of infection then twice a day for the following three days. Blood parasitaemias were estimated on the fourth day and compared with those of the untreated controls.

The results are given in Table 1, the results being expressed as percentage inhibition of *P. berghei*.

EXAMPLE 58

Monolayer cultures of chick embryo liver cells were seeded onto microtitration plates and treated with the test compound (formulated by suspension in ethanol (0.05 ml) followed by dilution with sterile water (0.95 ml). Sporozoites of *Eimeria tenella* in culture medium were added and the culture fixed 90 hours after infection. The percentage inhibition compared to controls was determined, the results being expressed on a scale of 0(0–10% inhibition) to 4(91–100% inhibition). The results are given in Table 2.

TABLE 1

| Compound (Example No.) | % inhibition | |
|---|---|---|
| | 7 × 10 mg/kg | 7 × 100 mg/kg |
| 1 | 65 | 100 |
| 2 | NT | 83 |
| 3 | 50(7 × 2.5) | NT |
| 4 | 67 | 97 |
| 6 | 55 | 99 |
| 7 | 46 | 99 |
| 8 | 89 | 100 |
| 9 | 32 | 89.6 |
| 10 | 85 | 99 |
| 11 | 54 | 99 |
| 13 | 77 | 100 |
| 14 | 77 | 100 |
| 15 | 4 | 86 |
| 16 | 81 | 100 |
| 17 | NT | 62 |
| 18 | NT | 95 |
| 19 | 52 | 99.9 |
| 20 | NT | 97.5 |
| 21 | 68 | 100 |
| 23 | 38 | 100 |
| 25 | 64 | 99.9 |
| 26 | 52 | 85(7 × 50) |
| 27 | 73 | 85 |
| 28 | NT | 53 |
| 29 | 47 | 100 |
| 30 | 59 | NT |
| 31 | 33 | NT |
| 32 | NT | 43 |
| 33 | 10 | NT |
| 34 | NT | 9(7 × 50) |
| 35 | NT | 39 |
| 36 | NT | 19 |
| 37 | 50 | 22 |
| 38 | 9 | 36 |
| 39 | 73 | 99.7 |

TABLE 1-continued

| Compound | % inhibition | |
|---|---|---|
| (Example No.) | 7 × 10 mg/kg | 7 × 100 mg/kg |
| 40 | 82 | 100 |
| 41 | NT | 100 |
| 42 | 93 | 100 |
| 43 | 24 | 60 |
| 44 | NT | 27 |
| 45 | 84 | 100 |
| 46 | NT | 98 |
| 48 | 22 | 88 |
| 49 | NT | 76 |
| 51 | 63 | NT |
| 52 | 95 | 100(7 × 50) |
| 53 | 43 | 100(7 × 50) |
| 56 | 100; (93at7 × 2) | NT |

NT = Not tested

TABLE 2

| | Index of Inhibition | |
|---|---|---|
| Compound Example No | 5 µg/ml | 20 µg/ml |
| 5 | 4+ | 4+ |
| 11 | NT | 4+ |
| 21 | NT | 2+ |
| 25 | 2+ | 3+ |
| 26 | 4+ | NT |
| 28 | 3+ | 4+ |
| 32 | NT | 2+ |
| 34 | 4+ | 4+ |

NT = Not Tested

EXAMPLE 60

1. The LD$_{50}$ of the compound of Example 3, both as the free base and the hydrochloride salt was determined in female rats by standard techniques the compound being administered as a 10% w/v suspension in corn oil orally by gavage. The results are given below.

| Compound | LD$_{50}$ |
|---|---|
| Example 3 - free base | 79.4 mg/kg |
| Example 3 - HCl salt | 63 mg/kg |

2. The LD$_{50}$ of the compound of Example 3 was determined in mice by standard techniques, the compound being administered orally in a suspension of 0.25% Celacol. An LD$_{50}$ of approximately 45 mg/kg was found.

EXAMPLE 61

| Tablet Formulation | |
|---|---|
| 3-(2-Amino-4-chlorophenylthiomethyl)-1,2,4-oxadiazole | 100 g |
| Lactose | 100 g |
| Starch | 30 g |
| Methylcellulose | 2 g |
| Magnesium Stearate | 2 g |

EXAMPLE 62

| Injectable Solution | | |
|---|---|---|
| 3-(2-Aminophenylthiomethyl)-1,2,4-oxadiazole hydrochloride | | 10.0 g |
| Chlorocresol | | 0.1 g |
| Water for injections | to produce | 100 ml |

EXAMPLE 63

| Dispersible Granules | Parts by weight |
|---|---|
| 3-(2-Methylaminophenylthiomethyl)-1,2,4-oxadiazole | 50 |
| Lactose | 49 |
| Povidone | 1 |

We claim:

1. A compound of the formula (I):

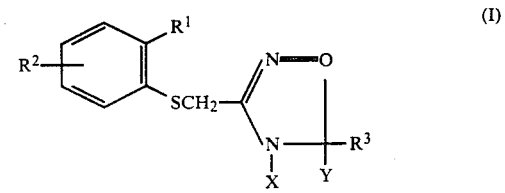

wherein R$^1$ is selected from the group consisting of amino or substituted amino;

each R$^2$ is the same or different, in one or more of the 3, 4, 5 or 6 positions and is selected from the group consisting of hydrogen, lower alkyl, halogen, hydroxy, alkoxy, alkylthio, arylthio, amino, substituted amino, cyano or nitro;

X and Y together represent a bond or X and Y are both hydrogen;

R$^3$ is selected from the group consisting of hydrogen, lower alkyl, aryl, and a group —SCH$_2$Ar; and Ar is phenyl, optionally substituted with one, two or three substituents which may be the same or different;

and acid addition salts thereof.

2. A compound of formula (I) according to claim 1 wherein R$^2$ is hydrogen.

3. A compound of the formula (II):

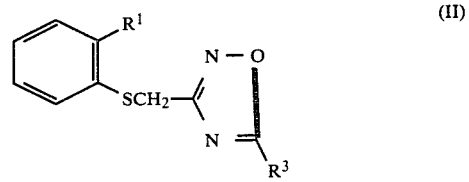

wherein R$^1$ is selected from the group consisting of amino and substituted amino;

R$^3$ is selected from the group consisting of hydrogen, lower alkyl, aryl, and a group —CH$_2$SAr; and Ar is phenyl optionally substituted with one, two or three substituents which may be the same or different;

and acid addition salts thereof.

4. A compound according to any of claims 1 to 3 wherein R$^1$ is selected from the group consisting of amino, alkylamino, amino alkyl amino, arylamino, aralkylamino, amido, alkoxycarbonylamino, sulphonamido, ureido, thioureido or imino.

5. A compound according to any one of claims 1 to 3 wherein R$^1$ is selected from the group consisting of NH$_2$, NHCH$_3$ and —N(CH$_3$)$_2$.

6. A pharmaceutical formulation for the treatment of protozoal infections comprising from 10 mg to 1 g of a compound as defined in any one of claims 1 to 5 or a pharmaceutically acceptable acid addition salt thereof, together with a pharmaceutically acceptable carrier therefor.

7. A veterinary formulation comprising for the treatment of protozoal infections in mammals or birds comprising 50 to 100% w/w of a compound as defined in any one of claims 1 to 5 or a pharmaceutically acceptable acid addition salt thereof and 0 to 50% of a veterinarily acceptable carrier therefor.

8. A method for the treatment of a protozoal infection in an animal including man, comprising administration of a non-toxic, anti-protozoal effective amount of a compound as defined in any one of claims 1 to 5.

9. 3-(2-Aminophenylthiomethyl)-1,2,4-oxadiazole or a pharmaceutically acceptable acid addition salt thereof.

10. A composition for use in treating protozoal infections in mammals or birds which comprises an antiprotozoal amount of the compound or salt of claim 9 and a carrier therefor which is acceptable to the mammal or bird being treated.

11. A method of treating protozoal infections in mammals or birds which comprises administering an antiprotozoal amount of the compound or salt of claim 9 to the mammal or bird.

12. 3-(2-Methylaminophenylthiomethyl)-1,2,4-oxadiazole or a pharmaceutically acceptable acid addition salt thereof.

13. A composition for use in treating protozoal infections in mammals or birds which comprises an antiprotozoal amount of the compound or salt of claim 12 and a carrier therefor which is acceptable to the mammal or bird being treated.

14. A method of treating protozoal infections in mammals or birds which comprises administering an antiprotozoal amount of the compound or salt of claim 12 to the mammal or bird.

15. 3-(2-Dimethylaminophenylthiomethyl)-1,2,4-oxadiazole or a pharmaceutically acceptable acid addition salt thereof.

16. A composition for use in treating protozoal infections in mammals or brids which comprises an antiprotozoal amount of the compound or salt of claim 15 and a carrier therefor which is acceptable to the mammal or bird being treated.

17. A method of treating protozoal infections in mammals or birds which comprises administering an antiprotozoal amount of the compound or salt of claim 15 to the mammal or bird.

* * * * *